United States Patent
Scholl et al.

(10) Patent No.: US 12,220,136 B2
(45) Date of Patent: Feb. 11, 2025

(54) REAMER DEVICE WITH INTEGRATED DEPTH GAUGING

(71) Applicant: Conventus Orthopaedics, Inc., Maple Grove, MN (US)

(72) Inventors: Christopher H. Scholl, West Chester, PA (US); Joseph Jackson, Wilmington, DE (US); Jason Cianfrani, Conshohocken, PA (US); Kevin Rzasa, Wilmington, DE (US); Tim Schmucker, Glenolden, PA (US)

(73) Assignee: Conventus Orthopaedics, Inc., Horsham, PA (US)

( * ) Notice: Subject to any disclaimer, the term of this patent is extended or adjusted under 35 U.S.C. 154(b) by 275 days.

(21) Appl. No.: 17/670,427

(22) Filed: Feb. 12, 2022

(65) Prior Publication Data
US 2023/0255650 A1    Aug. 17, 2023

(51) Int. Cl.
*A61B 17/16* (2006.01)
*A61B 17/17* (2006.01)
*A61B 90/00* (2016.01)

(52) U.S. Cl.
CPC ........ *A61B 17/162* (2013.01); *A61B 17/1662* (2013.01); *A61B 17/1703* (2013.01); *A61B 17/1717* (2013.01); *A61B 90/06* (2016.02); *A61B 2090/062* (2016.02)

(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/164; A61B 17/1655; A61B 17/1657; A61B 17/1662; A61B 17/1664; A61B 17/1666; A61B 17/1668; A61B 17/1675; A61B 17/1682; A61B 17/1684
See application file for complete search history.

(56) References Cited

U.S. PATENT DOCUMENTS

| | | | | |
|---|---|---|---|---|
| 5,261,818 A * | 11/1993 | Shaw | ....................... | A61C 3/02 433/165 |
| 5,429,504 A * | 7/1995 | Peltier | .................. | A61C 8/0089 433/165 |
| 5,562,673 A * | 10/1996 | Koblish | ............... | A61B 17/164 606/80 |
| 5,573,537 A * | 11/1996 | Rogozinski | ........ | A61B 17/7092 606/80 |
| 5,941,706 A * | 8/1999 | Ura | ........................... | A61C 3/02 433/165 |
| 6,258,093 B1 * | 7/2001 | Edwards | .............. | A61B 17/164 606/85 |

(Continued)

FOREIGN PATENT DOCUMENTS

| | | | | |
|---|---|---|---|---|
| EP | 2777553 A2 * | 9/2014 | ........... | A61B 17/164 |
| EP | 2777553 B1 * | 6/2017 | ........... | A61B 17/164 |

(Continued)

*Primary Examiner* — Eric S Gibson
(74) *Attorney, Agent, or Firm* — Ice Miller LLP

(57) ABSTRACT

A reamer device is used in the preparation of the fibula prior to the placement of an intramedullary nail. The reamer device features one or more indicating grooves on its cutting edges. These grooves can be visualized radiographically during reaming to confirm depth for the placement of syndesmotic implants through the intramedullary nail.

16 Claims, 6 Drawing Sheets

(56) References Cited

U.S. PATENT DOCUMENTS

| | | | | |
|---|---|---|---|---|
| 6,514,258 | B1* | 2/2003 | Brown | A61C 1/084 |
| | | | | 408/202 |
| 6,517,581 | B2* | 2/2003 | Blamey | A61B 17/1668 |
| | | | | 606/172 |
| 7,074,224 | B2* | 7/2006 | Daniels | A61B 17/1668 |
| | | | | 606/80 |
| 7,582,092 | B2* | 9/2009 | Jones | A61F 2/36 |
| | | | | 623/22.12 |
| 8,460,297 | B2* | 6/2013 | Watlington | A61B 17/1688 |
| | | | | 606/80 |
| 8,523,866 | B2* | 9/2013 | Sidebotham | A61B 17/1617 |
| | | | | 606/80 |
| 8,597,298 | B2* | 12/2013 | Daniels | A61F 2/36 |
| | | | | 606/80 |
| 8,708,618 | B2* | 4/2014 | Hobohm | B23D 77/00 |
| | | | | 408/1 R |
| 9,247,945 | B2* | 2/2016 | Major | A61B 17/164 |
| 10,952,780 | B1* | 3/2021 | Watts | A61B 17/8605 |
| 2006/0085005 | A1* | 4/2006 | Kenealy, III | A61C 8/0089 |
| | | | | 606/80 |
| 2014/0257295 | A1* | 9/2014 | Major | A61B 90/06 |
| | | | | 606/88 |
| 2014/0276843 | A1* | 9/2014 | Koay | A61B 17/16 |
| | | | | 606/80 |
| 2019/0358046 | A1* | 11/2019 | Ehmke | A61B 17/1775 |
| 2023/0255650 | A1* | 8/2023 | Scholl | A61B 17/1682 |
| | | | | 606/80 |

FOREIGN PATENT DOCUMENTS

| | | | | |
|---|---|---|---|---|
| JP | 2014171892 A | * | 9/2014 | A61B 17/164 |
| JP | 2015163217 A | * | 9/2015 | A61B 17/1637 |
| JP | 6391948 B2 | * | 9/2018 | A61B 17/164 |

* cited by examiner

REAMER DEVICE WITH INTEGRATED DEPTH GAUGING

TECHNICAL FIELD

The present teachings relate to intramedullary (IM) fixation. More particularly, the present teachings relate to an apparatus and a method for reaming a fibula in performing intramedullary fixation.

BACKGROUND

IM fixation devices can be placed as a treatment option for fibular fractures and other injuries. IM fixation involves the treatment of unstable fibula fractures with an intramedullary nail. Generally, intramedullary fixation devices for fibula fractures are complicated by the need to perform reliable fixation of the fibula while maintaining length and minimizing wound issues. During the preparation and placement of existing fibular intramedullary nails and associated syndesmotic fixation, there is the potential for the placement of those syndesmotic members too distally within the fibula, such that they cause damage to the intraarticular surfaces. Also, existing procedures are complicated by requiring increased intraoperative time to optimally place those fixation devices.

BRIEF SUMMARY OF THE DISCLOSED EMBODIMENTS

During the preparation and placement of existing fibular intramedullary nails and associated syndesmotic fixation, there is the potential for the placement of those syndesmotic members too distally within the fibula, such that they cause damage to the intraarticular surfaces. This issue is corrected intraoperatively by the subsequent re-placement of the intramedullary nail to avoid such an interference, which may contribute to increased operative time. This is solved in the presently disclosed embodiments by providing visualizable markers during the reaming step to confirm preliminary placement of those fixation members before the intramedullary nail is placed within the fibula.

According to some embodiments, a reamer device (also referred to as a "reamer") is provided as a surgical implement to ream a patient's bone during a procedure to implant a surgical component. The reamer device can include a cutting head that includes a plurality of helical cutting edges arranged to correspond with a configuration of the surgical component; one or more grooves on at least one of the helical cutting edges, each of the one or more grooves forming a depression at an outer surface of an associated helical cutting edge, and arranged on the cutting head at one or more radial distances from the longitudinal axis of the reamer; and a drive socket.

According to some embodiments, the reamer device is operable to ream an intramedullary canal of a patient's fibula during a surgical procedure to implant a distal stem component. In some embodiments, grooves are arranged on the helical cutting edges to enable a user to visually confirm depth of the surgical implement during the procedure. A drive socket on a proximal end of the reamer can be configured to be insertable into a chuck of a rotary actuator. According to some embodiments, the procedure may be used to insert an intramedullary nail.

According to some embodiments, an intramedullary reaming system operable to ream an intramedullary canal of a patient's fibula during a surgical procedure to implant a distal stem component can include a reamer device having a cutting head that includes a plurality of helical cutting edges arranged to correspond with the distal stem component; one or more grooves on at least one of the helical cutting edges, each of the one or more grooves forming a depression at an outer surface of an associated helical cutting edge, and arranged on the cutting head at one or more radial distances from the longitudinal axis of the reamer; and a drive socket. As described above, the reamer device is operable to ream an intramedullary canal of a patient's fibula during a surgical procedure to implant a distal stem component.

According to some embodiments, at least one groove of the helical cutting edge can form a depression having a depth of 0.65 mm to 0.85 mm from the helical cutting edge. For example, at least one groove can form a depression approximately 0.75 mm deep from the helical cutting edge. In some embodiments, one or more grooves of the helical cutting edge can form an associated depression centered at a distance of approximately 10 mm to 25 mm from a distal end of the head. In some embodiments, a cutting head can have grooves spaced at a distance of approximately 10 mm from each other. In one non-limiting example, a cutting head can include a first groove forming a first depression in an associated helical cutting edge, the first depression centered approximately 12.5 mm from the distal end of the cutting head and a second groove forming a second depression in an associated helical cutting edge centered approximately 22.5 mm from the distal end.

The intramedullary reaming system can further include a rotary actuator comprising a chuck configured to receive the drive socket. According to some embodiments, the intramedullary reaming system can include an intermedullary nail having one or more vias configured to receive one or more syndesmotic implants. Additionally, the system can include a fibular plate configured to facilitate entry of the one or more syndesmotic implants.

Also provided is a method for performing reaming of an intramedullary canal of a patient's fibula during a surgical procedure to implant a distal stem component, according to some embodiments. In the method, a user identifies a reaming starting point on a distal end of a fibula, and reams the fibula using a reamer device. As described above, the reamer device can include a cutting head that includes a plurality of helical cutting edges arranged to correspond with the distal stem component; and one or more grooves on at least one of the helical cutting edges, each of the one or more grooves forming a depression at an outer surface of an associated helical cutting edge, and arranged on the cutting head at one or more radial distances from the longitudinal axis of the reamer. The grooves arranged on the helical cutting edges allow a user to obtain visual confirmation of the position of at least one of the grooves within the fibula. According to some embodiments, the position of the grooves identifies an appropriate depth for optimal placement of one or more lateral screws, syndesmotic implants, or other fixation implants. Radiographic imaging can be performed to identify a location of at least one of the grooves. The method can further include inserting an intermedullary device having one or more vias configured to receive one or more syndesmotic implants, according to some embodiments. Additionally, adjustment can be performed to optimize alignment of the intramedullary device based on the radiographic image. According to some embodiments, the method can further include inserting one or more lateral screws, syndesmotic implants, or other fixation implants aligned with a via of the one or more vias.

DETAILED DESCRIPTION OF THE DISCLOSED EMBODIMENTS

Embodiments may be implemented in hardware, firmware, software, or any combination thereof. Reaming of bones is practiced to allow the insertion of intramedullary nails. However, the process as performed in the prior art can cause complications. The embodiments shown in the exemplary methods and device are not exhaustive and other operations can be performed in addition to the illustrated processes. In some embodiments of the present disclosure, the operations may vary and/or can be performed in a different order.

Reamer Device with Visual Inspection Grooves

Figure 1:
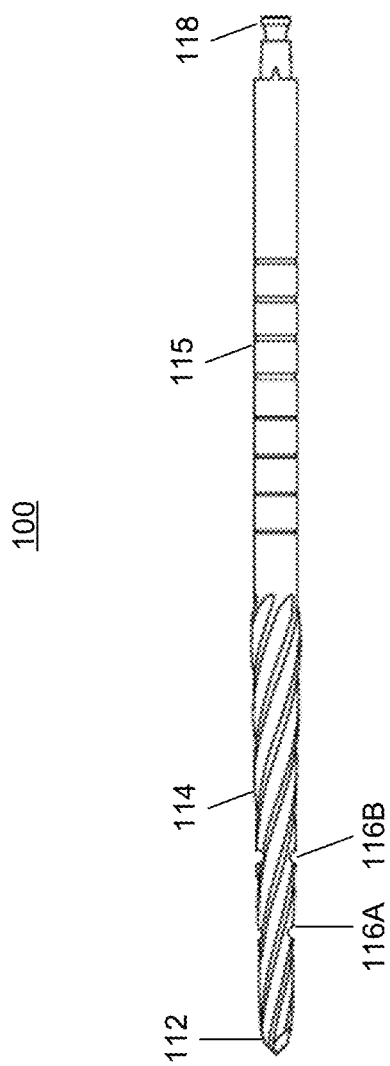
FIG. 1 is an illustration of a reamer device, according to some embodiments.

FIG. 1 illustrates a reamer device 110 for performing an operation to ream a bone, such as a fibula. According to some embodiments, reamer device 110 corresponds an intramedullary nail having one or more depth gauges to indicate an appropriate depth that has been achieved during a reaming procedure. Specifically, reamer device 110 includes a cutting tip 112, one or more helical cutting edges 114 with flutes formed therebetween, and one or more grooves 116 (e.g., grooves 116A and 116B). The sharp cutting tip 112 bores through bone, while the helical cutting edges 114 can traverse the bone while corresponding to geometrical patterning of an intramedullary component. According to some embodiments, reamer device 110 may be a cannulated tapered reamer device. Reamer device 110 can be formed from stainless steel, cobalt chrome, or titanium, or other metals or alloys suitable for medical use, to name just a few non-limiting examples.

Grooves 116 allow for precise control over alignment and position of the reamer device 110 during a bone reaming procedure. Specifically, grooves 116 enable a user (e.g., a health care practitioner or the like) to visually confirm during the reaming step that an appropriate depth has been prepared to allow for optimal placement of syndesmotic fixation. In existing technology, there is the potential of increased intraoperative time to optimally place those fixation members. In an embodiment, syndesmotic fixation members can be placed accurately, thereby minimizing or eliminating additional intraoperative time by performing a visual check of the position of the grooves 116 during performance of the reaming step.

During the visual check, the user (e.g., a health care practitioner, or the like) performs a radiographical scan of the reaming to confirm the depth of the reaming that has been performed by visually sighting grooves (e.g., 116A and 116B) on the cutting edges of the reamer device 100. Anterior-Posterior (AP) radiographs, lateral radiographs, and the like, can be performed during the visual check to determine the depth of grooves 116 (and correspondence of groove depth to the site of the fracture, for example).

According to some embodiments, one or more grooves 116 form a depression in a radial outer surface of an associated helical cutting edge. According to some embodiments, the depression can have a depth of between zero and 1 millimeter (mm) to the helical edge. According to some embodiments, at least one of grooves 116 of the helical cutting edge can form a depression having a depth of 0.65 mm to 0.85 mm from the helical cutting edge. For example, at least one groove can form a depression approximately 0.75 mm deep from the helical cutting edge.

According to some embodiments, one or more grooves 116 may be arranged at one or more radial distances from the longitudinal axis of the cutting tip 112. According to some embodiments, one or more grooves 116 may be arranged at a distance d from a distal end of the cutting edge, where d is a distance between 10 and 25 mm. In some embodiments, a cutting head can have grooves 116 spaced at a distance of approximately 10 mm from each other. In one non-limiting example, a cutting head (e.g., tip 112) can include a first groove 116A forming a first depression in an associated helical cutting edge 114, the first depression centered approximately 12.5 mm from the distal end of the cutting head and a second groove 116B forming a second depression in an associated helical cutting edge 114 centered approximately 22.5 mm from the distal end.

Reamer device 100 can include a body 115 at a proximal end adjacent to the one or more cutting edges 114. In some embodiments, reamer device 100 can include a connector 118 formed at the proximal end of body 115, wherein the connector 118 is constructed and arranged to be coupled to a rotary actuator (e.g., a rotary power tool having a power source, a manual rotary driver, or the like), as further described hereinbelow in relation to FIG. 3. The connector 118 can be coupled to the rotary actuator by insertion into a chuck thereof. In some embodiments, connector 118 can be reduced dimensionally relative to the body to fit into the chuck of a rotary power tool. In other embodiments, connector 118 can be flatted or tanged to prevent slipping in the chuck.

Figure 2:
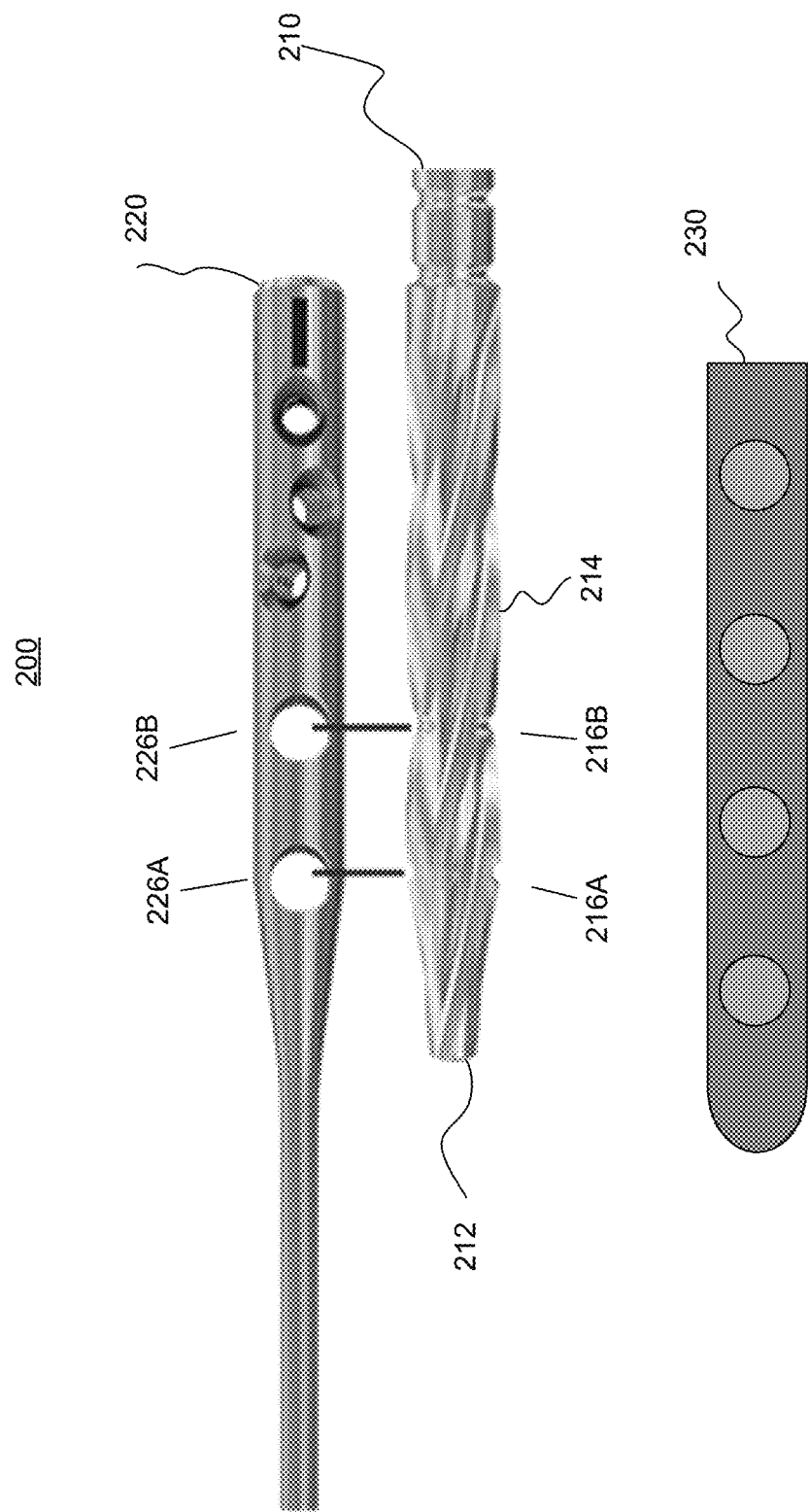
FIG. 2 illustrates a reaming system including a reamer device, according to some embodiments.

FIG. 2 illustrates an intramedullary nail system 200 that includes a reamer device 210, which may be an embodiment of reamer device 110 and corresponds to intramedullary nail 220 as described in greater detail hereinbelow. The stabilization of bone fractures can be achieved through reaming the medullary cavity using reamer device 210 and inserting intramedullary nail 220 therein. In some embodiments, the insertion of intramedullary nail 220 can include locking bolts (not shown). In other embodiments, locking bolts are not necessary. According to embodiments, reamer device 210 can minimize breakage of the interlocking screws and improve bone union at the fracture site.

As described above, reamer device 210 includes a cutting tip 212, one or more helical cutting edges 214, and one or more grooves 216, such as the grooves 216A and 216B. According to some embodiments, reamer device 210 may be a cannulated tapered reamer device. As depicted in FIG. 2, grooves 216 are formed on cutting edges 214 of the reamer device 210, wherein the vertical lines indicate how the grooves 216A and 216B align with the corresponding syndesmotic fixation holes 226A and 226B on the intramedullary nail 220. The reamer device 210 may be used prior to the placement of the nail, and radiographic visualization of the grooves 216 during the reaming process provides a visual aid to the user to identify where the user can expect the syndesmotic fixation to be placed after the intramedullary nail 220 is in place.

Grooves 216 allow for precise control over alignment and position of the reamer device 210 during a bone reaming procedure. As discussed above, grooves 216 may be aligned with a one or more syndesmotic fixation holes 226 of intramedullary nail 210. In one non-limiting example, one or more screws may be fixed between the tibia and fibula in a syndesmotic fixation procedure to stabilize the syndesmosis until syndesmotic ligament healing can be achieved. A syndesmotic screw is a positioning screw that is used to hold the syndesmosis without compression. In some embodiments, the syndesmotic screw is positioned through a fibular plate 230. The fibular plate 230 is positioned along a posterolateral fibular border to facilitate entry of a syndesmotic screw into a tibia.

Figure 3:
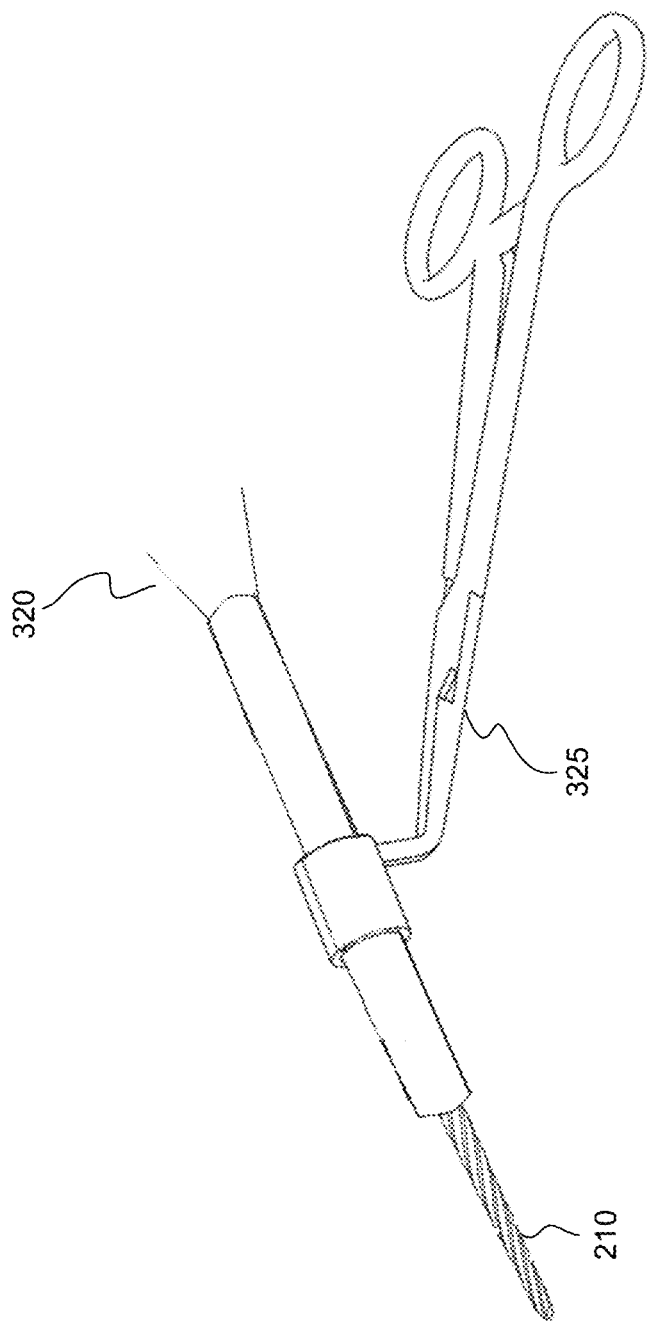
FIG. 3 illustrates a reamer device coupled to a rotary actuator, according to some embodiments.

FIG. 3 illustrates a reamer device 210 coupled to a rotary actuator 320.

The body of reamer device 210 is inserted into a chuck of a rotary actuator 320. According to some embodiments, reamer device 210 and/or rotary actuator 320 may be clasped using a clasping device 325. During a procedure, a user may precisely guide reamer device 210 into a targeted bone utilizing clasping device 325. The user may monitor radiograph images while performing the procedure and while securely clasping reamer device 210. In this manner, precise control of the depth of the reaming can be performed to correspond with an arrangement of syndesmotic fixation holes in an intramedullary nail.

Figure 4A:
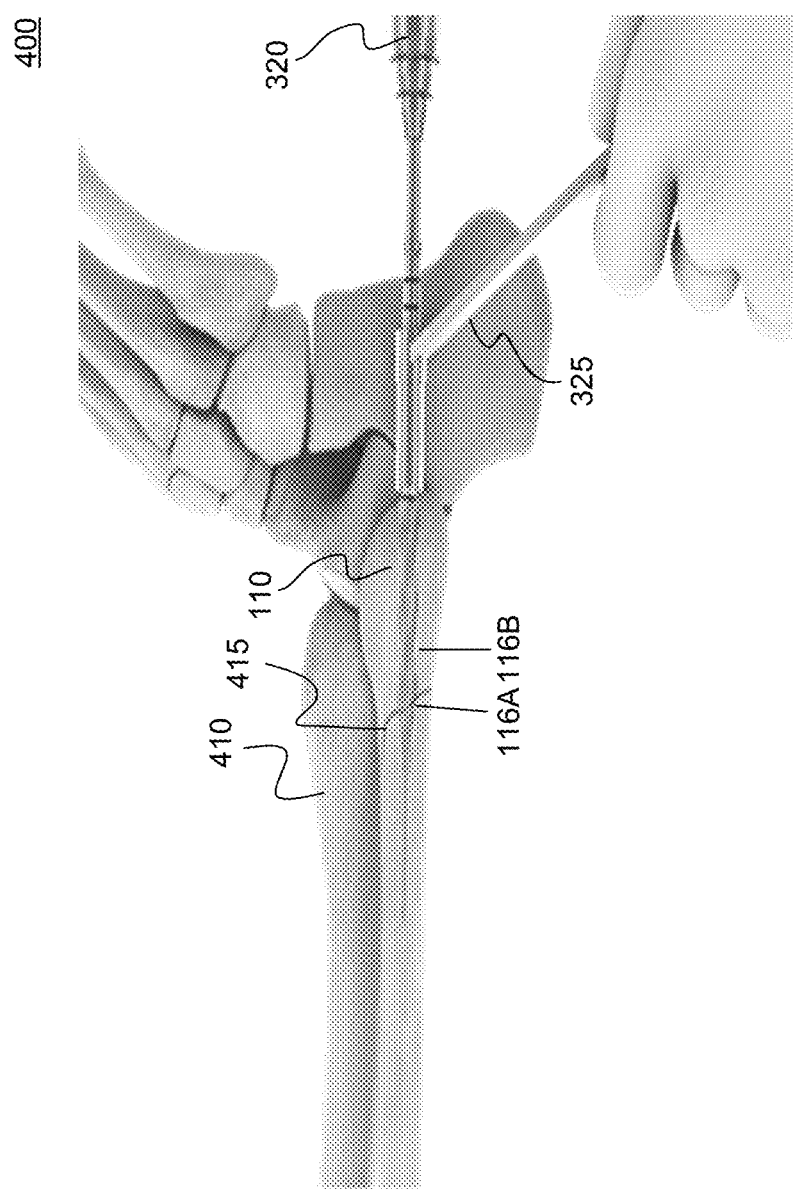
FIG. 4A depicts radiographic visualization of a reamer device, including confirmation of depth based on a position of grooves on the reamer device, according to some embodiments.
Figure 4B:
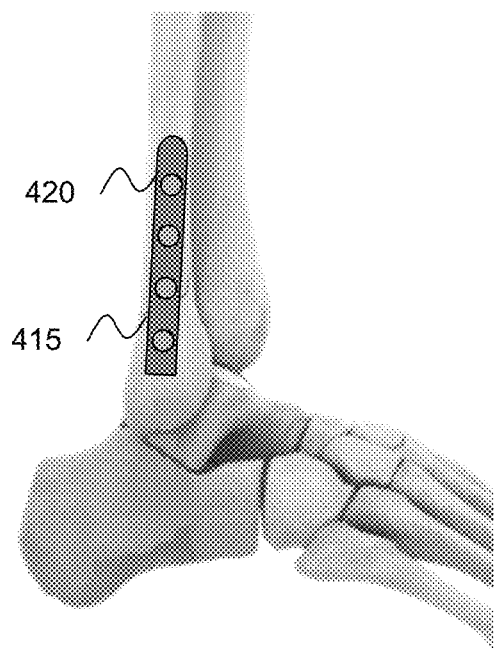
FIG. 4B depicts placement of a fibular plate for use in syndesmotic fixation procedures, according to some embodiments.

FIG. 4A illustrates radiographic visualization 300 of a reamer device 110, including confirmation of depth based on a position of grooves 116 during reaming as described above. A user performing a surgical reaming procedure, such as a syndesmotic fixation procedure, can utilize radiographic visualization 400 of reamer device 110 to guide the procedure, including how far to insert reamer device 110 into the targeted bone. The user can visually confirm the depth of the reaming that has been performed utilizing the radiographical scan by visually sighting grooves (e.g., 116A and 116B) on the cutting flutes of the reamer device 100. Anterior-Posterior (AP) radiographs, lateral radiographs, and the like, can be performed during the visual check to determine the depth of grooves 116 (and correspondence of groove depth to the site of the fracture 415, for example). FIG. 4B illustrates the placement of a fibular plate 230 along a posterior border along the back of the fibula, which can be aligned with intramedullary nail 230 to facilitate entry of a syndesmotic screw into the tibia. For example, after insertion of intramedullary nail 220, a user can fix a syndesmotic screw through the fibular plate and intramedullary nail 230 to the tibia utilizing fibular plate 420 to hold but not compress the syndesmosis.

Figure 5:
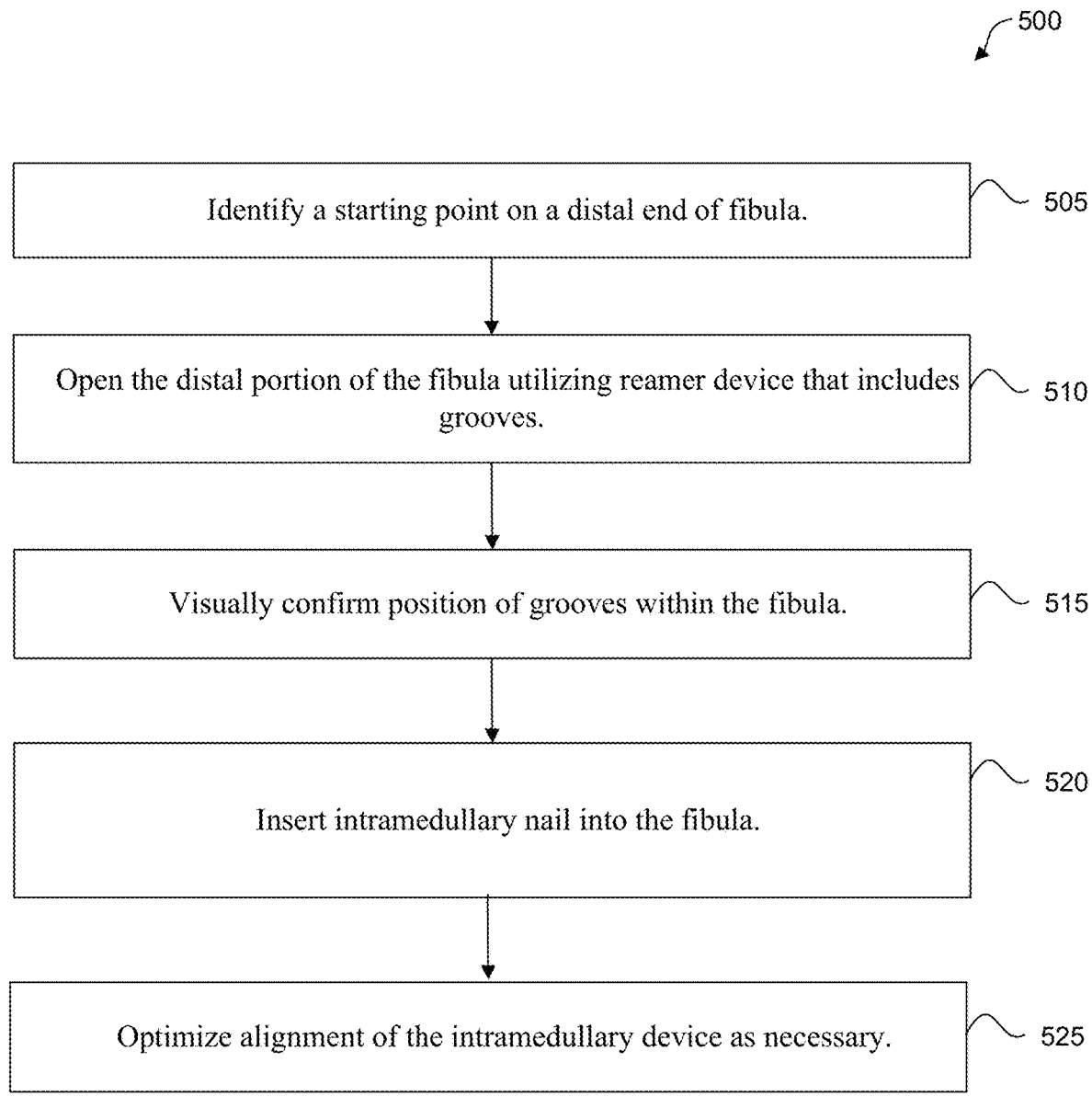
FIG. 5 is a flow diagram of a method for performing reaming and intramedullary nail insertion, according to some embodiments.

Performing Intramedullary (IM) Fixation Using Reamer Device with Visual Inspection Grooves FIG. 5 depicts a flow diagram of a method for performing a surgical procedure 500 to drive a reaming device to a confirmed depth, according to some embodiments.

Referring to FIG. 5, surgical procedure 500 includes an operation 505 of identifying a starting point on a distal end of a fibula. For example, the starting point can be confirmed by a user of reamer device 110 (e.g., a health care practitioner, or the like). The starting point may be on a distal tip of the fibula in some embodiments. According to some embodiments, the starting point may be slightly medial to the most distal portion of the fibula on the AP view. On the lateral view, it is slightly anterior to the center of the fibular canal.

In some embodiments, operation 505 can include insertion of a guide wire from the distal tip into the intramedullary canal to preserve the lateral cortex of the fibula during reaming According to some embodiments, a guide wire having a 0.062-inch gauge can be used.

A reamer device 110 having a 6.2 mm length can be used. According to some embodiments, a tissue protector can be used to prevent injury while driving the reamer device. For example, a patient may be prepared for surgery, including placing the patient under general anesthesia or sedation, administering antibiotics, and placing the patient on an operating room table. A radiographic/fluoroscopic imaging device can be directed toward the site of the procedure. According to some embodiments, a guide wire can be driven into the talus. A skin incision can be made to the tip of the fibula.

According to some embodiments, distal reaming can be performed. For example, a 6.2 mm tapered reamer device can be driven over a guidewire through a tissue protector until the reamer device flutes are fully within the bone, as confirmed by visual inspection of grooves 116 using one or more radiographs. According to other embodiments, proximal reaming can be performed. In another non-limiting example, a 3.2 mm reamer device can be driven over the guidewire and through the tissue protector, until grooves 116 are well within the bone.

Procedure 500 continues with operation 510, in which the reamer device 110 is driven over the guide wire to open the distal portion of the fibula (a measurement of the distal portion can vary). For example, a 6.2 mm tapered reamer device may be driven over the guidewire through the tissue protector until the reamer device flutes are fully within the bone. As described in detail above, reamer device 110 includes grooves 116 permitting the user to visually confirm the depth and alignment of reamer device 110 during a bone reaming procedure.

At operation 515, the user can visually confirm, using radiograph images, the position of grooves 116 within the fibula, verifying that an appropriate depth has been prepared to allow for optimal placement of syndesmotic fixation. In existing technology, there is the potential of increased intraoperative time to optimally place those fixation members. In an embodiment, syndesmotic fixation members can be placed accurately, thereby minimizing or eliminating intraoperative time by performing one or more visual checks during performance of the reaming step.

For example, at 515, the user can perform a radiographical scan of the reaming to confirm the depth of the reaming that has been performed by visually sighting grooves (e.g., 116A and 116B) on the cutting flutes of the reamer device 100. According to some embodiments, fluoroscopy is performed to enable the visual inspection. According to some embodiments, Anterior-Posterior (AP) radiographs, lateral radiographs, and the like, can be performed during the visual check to determine the depth of grooves 116 (and correspondence of groove depth to the site of the fracture, for example).

At operation 520, intramedullary nail 120 is inserted into the fibula.

According to some embodiments, the tissue protector and guide wire can be removed at 520 before or after insertion of intramedullary nail 120. According to some embodiments, a visual check as described above (e.g., guided by fluoroscopy) can be performed while intramedullary nail 120 is inserted into the bone. According to some embodiments, intramedullary nail 120 can be rotated to allow for the anatomic placement of lateral screws, syndesmotic fixation, or other fixation into the tibia.

At operation 525, after intramedullary nail 120 is inserted into the fibula, proximal/distal adjustments may be made to optimize alignment of the intramedullary device.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments but should be defined only in accordance with the following claims and their equivalents.

What is claimed is:

1. A surgical implement operable to ream a patient's bone during a procedure to implant a surgical component, the surgical implement comprising:
    a cutting head that includes a plurality of helical cutting flutes arranged to correspond with a configuration of the surgical component; and
    one or more grooves formed into at least one of the helical cutting flutes, each of the one or more grooves forming a depression at an edge of an associated helical cutting flute, and arranged at one or more radial distances from a longitudinal axis of the cutting head, wherein the cutting head and the one or more grooves are positioned and dimensioned such that, when the reamer device is inserted into an intramedullary canal, the depression of the one or more grooves is structurally aligned with a syndesmotic fixation hole of the surgical component.

2. The surgical implement of claim 1, wherein the surgical implement is operable to ream an intramedullary canal of a patient's fibula during a surgical procedure to implant the surgical component.

3. The surgical implement of claim 1, wherein the one or more grooves are arranged to enable a user to visually confirm a depth of the surgical implement during the surgical procedure.

4. The surgical implement of claim 1, further comprising a drive socket configured to be insertable into a chuck of a rotary actuator.

5. The surgical implement of claim 1, wherein the surgical component is an intramedullary nail.

6. The surgical implement of claim 1, wherein at least one groove forms a depression in an associated helical cutting flute at a depth between zero and 1 millimeter (mm).

7. The surgical implement of claim 6, wherein the depth is approximately 0.75 mm.

8. The surgical implement of claim 1, wherein at least one groove is arranged at a distance d from a distal end of a cutting edge, wherein d is between 10 and 25 mm.

9. The surgical implement of claim 8, wherein a first groove is arranged at a distance d1 from a distal end of the cutting edge and a second groove is arranged at a distance d2 from the distal end, wherein d1 is approximately 12.5 mm and d2 is approximately 22.5 mm.

10. An intramedullary reaming system operable to ream an intramedullary canal of a patient's fibula during a surgical procedure to implant a surgical component, the intramedullary reaming system comprising:
    a reamer device comprising:
        a cutting head that includes a plurality of helical cutting flutes arranged to correspond with the surgical component, wherein the;
        one or more grooves formed into at least one of the helical cutting flutes, each of the one or more grooves forming a depression at an edge of an associated helical cutting flute, and arranged at one or more radial distances from a longitudinal axis of the cutting head, wherein the cutting head and the one or more grooves are positioned and dimensioned such that, when the reamer device is inserted into the intramedullary canal, the depression of the one or more grooves is structurally aligned with a syndesmotic fixation hole of the surgical component;
    a drive socket; and
    a rotary actuator comprising a chuck, wherein the chuck is configured to receive the drive socket.

11. The intramedullary reaming system of claim 10, wherein the surgical component comprises an intermedullary nail having one or more vias configured to receive one or more syndesmotic implants.

12. The intramedullary reaming system of claim 11, further comprising a fibular plate, wherein the fibular plate is configured to facilitate entry of the one or more syndesmotic implants.

13. The intramedullary reaming system of claim 10, wherein the reamer device is operable to ream an intramedullary canal of a patient's fibula during a surgical procedure to implant the surgical component.

14. The intramedullary reaming system of claim 10, wherein the surgical component is an intramedullary nail.

15. The intramedullary reaming system of claim 10, wherein at least one groove forms a depression in an associated helical cutting flute at a depth between zero and 1 millimeter (mm).

16. The intramedullary reaming system of claim 10, wherein at least one groove is arranged at a distance d from a distal end of a cutting edge, wherein d is between 6 and 10 mm.

* * * * *